(12) United States Patent
Saito et al.

(10) Patent No.: US 6,676,960 B2
(45) Date of Patent: Jan. 13, 2004

(54) INTRAORAL ADHESIVE PREPARATION (75) Inventors: Junichi Saito, Ibaraki (JP); Kazuhisa Ninomiya, Ibaraki (JP); Masaaki Ito, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 236 days.

(21) Appl. No.: 09/940,946

(22) Filed: Aug. 28, 2001

(65) Prior Publication Data
US 2002/0071860 A1 Jun. 13, 2002

(30) Foreign Application Priority Data
Aug. 31, 2000 (JP) .......................... 2000-263623

(51) Int. Cl.[7] .......................... A61F 13/02; A61F 13/00; A61L 15/16
(52) U.S. Cl. .......................... 424/448; 424/49; 424/449
(58) Field of Search .......................... 424/448; 428/213, 428/296.7, 337, 323

(56) References Cited

U.S. PATENT DOCUMENTS

| | | | | |
|---|---|---|---|---|
| 4,719,226 A | * | 1/1988 | Otsuka et al. | 514/449 |
| 5,759,926 A | * | 6/1998 | Pike et al. | 442/333 |

FOREIGN PATENT DOCUMENTS

| | | |
|---|---|---|
| EP | 1 034 781 A2 | 9/2000 |
| JP | 09 310259 | 12/1997 |
| JP | 10 331063 | 12/1998 |

* cited by examiner

Primary Examiner—Thurman K. Page
Assistant Examiner—Micah-Paul Young
(74) Attorney, Agent, or Firm—Leydig, Voit & Mayer, Ltd.

(57) ABSTRACT

An intraoral adhesive preparation is provided, which contains a support made of a nonwoven fabric mainly made of split type conjugated fibers, and an adhesive plaster layer containing a drug, which is formed on the support, wherein the split type conjugated fiber has an about triangular sectional shape after splitting, where the about triangle has the longest diameter ($D_L$) of 5 μm–15 μm, and the longest line segment ($D_S$) that vertically crosses the longest diameter of 2 μm–10 μm.

6 Claims, 3 Drawing Sheets

INTRAORAL ADHESIVE PREPARATION

TECHNICAL FIELD OF THE INVENTION

The present invention relates to an adhesive preparation to be applied to the oral cavity for intraoral administration of a drug.

BACKGROUND OF THE INVENTION

Conventional preparations for intraoral drug administration include liquid, ointment, jelly, spray and the like. In these preparations, unnecessary leakage of a drug into saliva and migration of the drug into the sites where the drug is not needed is inevitable, because the solution flows, base materials of ointment and jelly dissolve, a spray may be excessively applied and for other reasons. As a result, these preparations are associated with problems in that patients unnecessarily suffer from uncomfortableness, such as bitterness and the like, the rate of utilization of the drug decreases, preventing sufficient drug efficacy, and the like.

There has been recently proposed an intraoral adhesive preparation comprising a water-soluble or water-swellable polymer as a base of an adhesive layer containing a drug, as a preparation having superior adhesive property even on oral mucosa wet with water (e.g., saliva etc.). The proposed intraoral adhesive preparation may be inconvenient as are conventional preparations, because the adhesive layer dissolves or swells with time upon contact with saliva etc. and may come off and fall or the drug may leak and is washed away upon dissolution or swelling.

In recent years, moreover, various percutaneous absorption type pharmaceutical products conatining a pressure-sensitive adhesive have been devised and widely used for integumentary drug administration. Such percutaneous absorption type pharmaceutical products include various embodiments, wherein a typical one is an adhesive sheet type preparation consisting of a pressure-sensitive adhesive layer containing a drug and a polyester film support layer. If this adhesive sheet type preparation has a suitable adhesive power to the oral mucosa, the polyester film would sufficiently block the contact of the adhesive layer with saliva and prevent unnecessary uncomfortableness due to bitterness and the like felt by patients, or decrease in the drug utilization, which could lead to insufficient drug efficacy, because the pressure-sensitive adhesive layer is free of dissolution or leakage of the drug.

Nevertheless, the above-mentioned adhesive sheet type preparation has not been put to practical use for intraoral application. This is because a polyester film used for the above-mentioned adhesive sheet type percutaneously absorptive preparation is considerably stiff even if it is only about 12 $\mu$m thick, has many irregularities, and when applied to the oral cavity, where sensitivity is sharp, cannot sufficiently follow curves, which in turn results in poor adhesion and marked uncomfortableness. A thin film is also poor in handling property, making application of the sheet inside the oral cavity not an easy job.

On the other hand, a preparation including a flexible film as a support, such as polyethylene, vinyl chloride and the like, shows fine followability to curves, improving adhesion to the application site, but its flexibility degrades handling property and makes its application inside the oral cavity difficult. A flexible film tends to allow migration of the drug into the inside of a film, making the drug instable.

SUMMARY OF THE INVENTION

It is therefore an object of the present invention to provide an intraoral adhesive preparation, wherein an anchor effect of a support and an adhesive plaster layer is fine, adhesion to the surface having irregularities is fine due to superior flexibility, obliterating uncomfortableness such as stiffness, handling property is fine even in a narrow site such as in the oral cavity, and the drug hardly leaks out and is washed away due to saliva.

Accordingly, the present invention provides the following.

The intraoral adhesive preparation of the present invention comprises a support made of a nonwoven fabric mainly made of split type conjugated fibers, and an adhesive plaster layer containing a drug, which is formed on the support, wherein the split type conjugated fiber has an about triangular sectional shape after splitting, where the about triangle has the longest diameter ($D_L$) of 5 $\mu$m–15 $\mu$m, and the longest line segment ($D_S$), that vertically crosses the longest diameter, of 2 $\mu$m–10 $\mu$m. The inventive sheet achieves the above-mentioned objects.

In a preferable embodiment, a $D_L/D_S$ ratio is 1.5–2.5.

In a preferable embodiment, the above-mentioned split type conjugated fiber is obtained by splitting a conjugated fiber consisting of at least two kinds of fiber materials combined radially from the about center of the section, wherein the number of split is not less than 16.

In a preferable embodiment, the above-mentioned nonwoven fabric contains 1 to 50 undivided split type conjugated fibers in a 0.1 mm$^2$ section.

In a preferable embodiment, the above-mentioned nonwoven fabric has a thickness of 300–600 $\mu$m, and a density of 0.17–0.25 g/cm$^3$.

In a preferable embodiment, the above-mentioned intraoral adhesive preparation has a shorter diameter of 0.5–1.5 cm and a longer diameter of 1–3 cm.

In the context of the present invention, the term "about triangle" means a triangle in a wide sense, which includes not only mathematical triangle, but about fan, a triangular shape having any one of the sides curved to form a concave or convex, a triangular shape having round triangle apexes resembling a polygon, and the like.

In the present invention, of the line segments from the apex of the about triangle, which is the center of the split type conjugated fiber before division, to the arc of the about triangle (fan shape) forming the outer periphery of the split type conjugated fiber before division, the longest line segment is the longest diameter (length thereof $D_L$). Of the line segments vertically crossing the longest diameter and crossing the circumference of the triangle, the longest line has a length of $D_S$.

In the present invention, the term, "split type conjugated fiber" means a conjugated fiber obtained by compounding and spinning of two or more polymer components having different properties, using a spinneret divided in a predetermined number. The split type conjugated fiber is divided into thinner fibers by extracting one polymer component or by applying a strong impact (i.e., high pressure water stream), like sections of orange get separated when it is cut in thin slices.

DETAILED DESCRIPTION OF THE INVENTION

The present invention is described in more detail in the following.

The intraoral adhesive preparation of the present invention comprises a support made of a nonwoven fabric mainly made of split type conjugated fibers, and an adhesive plaster layer containing a drug, which is formed on the support.

The fiber material of the split type conjugated fiber used in the present invention is not particularly limited as long as a split type conjugated fiber can be formed. To be specific, a split type conjugated fiber made of two or more kinds of fiber materials obtained from viscose rayon, cuprammonium rayon, diacetate, triacetate, nylon, poly(vinylidene chloride), poly(vinyl alcohol), poly(vinyl chloride), polyester, polyacrylonitrile, polyethylene, polypropylene, polyurethane, polyalkylene paraoxybenzoate, polychlal (1:1 mixture of vinyl chloride and poly(vinyl alcohol)) and the like is used. Particularly, a split type conjugated fiber mainly composed of polyolefin, such as polyethylene, polypropylene and the like, more preferably polypropylene and polyester, is preferably used from the aspects of safety, stability, economic aspect and the like.

In the present invention, the sectional shape after dividing a split type conjugated fiber is an about triangular shape, where the about triangle has the longest diameter ($D_L$) of 5 $\mu$m–15 $\mu$m, preferably 7–13 $\mu$m, and the longest line segment ($D_S$), that vertically crosses the longest diameter, of 2 $\mu$m–10 $\mu$m, preferably 4–8 $\mu$m. When $D_L$ and $D_S$ are shorter than the above-mentioned ranges, the fiber becomes thinner and the flexibility too high, which in turn degrades handling property of the obtained intraoral medical adhesive sheet. In addition, since the clearance between fibers is too narrow, the adhesive plaster layer does not invade sufficiently and the anchor effect becomes lower. When it is longer than the above-mentioned ranges, the fiber becomes thick and the flexibility is degraded. As a result, the obtained intraoral adhesive preparation causes unpleasant sense of foreign substance upon adhesion.

The ratio ($D_L/D_S$) of the above-mentioned $D_L$ and $D_S$ is preferably 1.5–2.5, more preferably 1.7–2.3. When the $D_L/D_S$ ratio is smaller than 1.5, the fiber has an equilateral triangulate sectional shape, providing a wider clearance between the fibers. This causes too high a flexibility, thus degraded handling property of the obtained intraoral adhesive preparation. When the $D_L/D_S$ ratio is larger than 2.5, the fiber has a flattened sectional shape, which prevents sufficient interlacing of fibers, and tends to show poor feeling.

The split type conjugated fiber used in the present invention has a sectional shape after splitting of an about triangular shape, and shows a non-crimp tendency. Therefore, a dense nonwoven fabric having a higher fiber density can be obtained. In addition, since the area of a nonwoven fabric surface in contact with the adhesive plaster layer is large, the adhesive plaster layer shows superior adhesive property to a nonwoven fabric. Because the about triangle has the longest diameter ($D_L$) of 5 $\mu$m–15 $\mu$m, and the longest line segment ($D_S$) that vertically crosses the longest diameter of 2 $\mu$m–10 $\mu$m, an adhesive plaster layer can desirably enter the gaps between suitably dense fibers to show a fine anchor effect and appropriate stiffness while maintaining flexibility. When the $D_L/D_S$ ratio is set to 1.5–2.5, the above-mentioned properties can be expressed as desired.

As a typical nonwoven fabric for pharmaceutical products, there are mentioned a stretch nonwoven fabric obtained by interlacing a crimped fiber, such as polyester and the like, which is a base fabric for stretch poultice, by a needle punch method or a spun lace method. This nonwoven fabric comprises fibers mutually interlaced in coil crimps and has an about circular fiber cross-section. This affords high stretcheability and superior flexibility. However, most of the fabric of this type has a fiber diameter of not less than 15 $\mu$m. This has a consequence that the fibers on the surface of the nonwoven fabric, that comes in contact with the adhesive plaster layer, are rather dispersed as compared to the fibers of the split type conjugated fiber, which makes the anchor effect insufficient depending on the kind of plaster. In addition, the nonwoven fabric used as a base fabric of poultice generally has a thickness of not less than 800 $\mu$m, an intraoral adhesive preparation using such fabric causes considerable sensation of foreign matter depending on the adhesion site. Moreover, since a stretch nonwoven fabric is highly flexible and limp, and therefore, an intraoral adhesive preparation using this fabric shows markedly degraded handling property depending on the size of the intraoral adhesive preparation.

Figure 1:
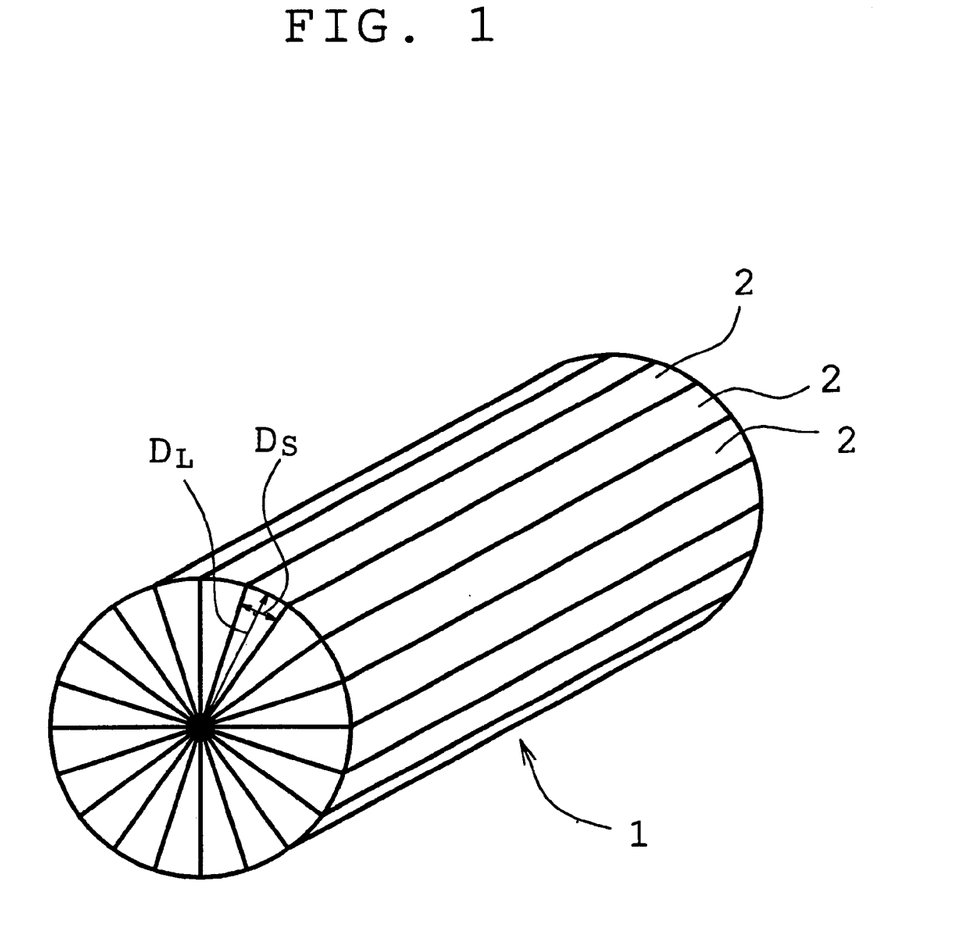
FIG. 1 schematically shows one embodiment of the split type conjugated fiber used in the present invention.

FIG. 1 schematically shows one embodiment of the split type conjugated fiber used in the present invention. The split type conjugated fiber 1 is obtained by dividing, in a predetermined number, a conjugated fiber comprising two or more fiber materials arranged radially from the approximate center of the about circular section, and has, about the central axis, plural divisions 2 having an about triangular shape. The split type conjugated fiber 1 has a structure wherein divisions 2 consisting of each fiber material alternately appear in the circumferential direction. The above-mentioned split type conjugated fiber 1 is obtained by, for example, the following method. Using a spinneret having inside divisions in a predetermined number, two or more kinds of polymer components having different properties (these polymer components constituting each fiber material) are composite spun and other method. The number of the above-mentioned division is generally 8 or 16. In the present invention, it is preferably 16 or more, more preferably 20 or more. When the number of the above-mentioned divisions is less than 16, a split type conjugated fiber having a desirable $D_L/D_S$ ratio is hard to obtain.

The fiber diameter and fiber length of the split type conjugated fiber 1 is not particularly limited and a fiber having a fiber diameter of 20–22 $\mu$m and a fiber length of about 40 mm is preferably used. The sectional shape of the split type conjugated fiber 1 is not limited to a circle, and may be about ellipse. Moreover, the method for dividing the split type conjugated fiber is not particularly limited and, for example, it can be divided by soaking a split type conjugated fiber in a water stream.

Figure 2:
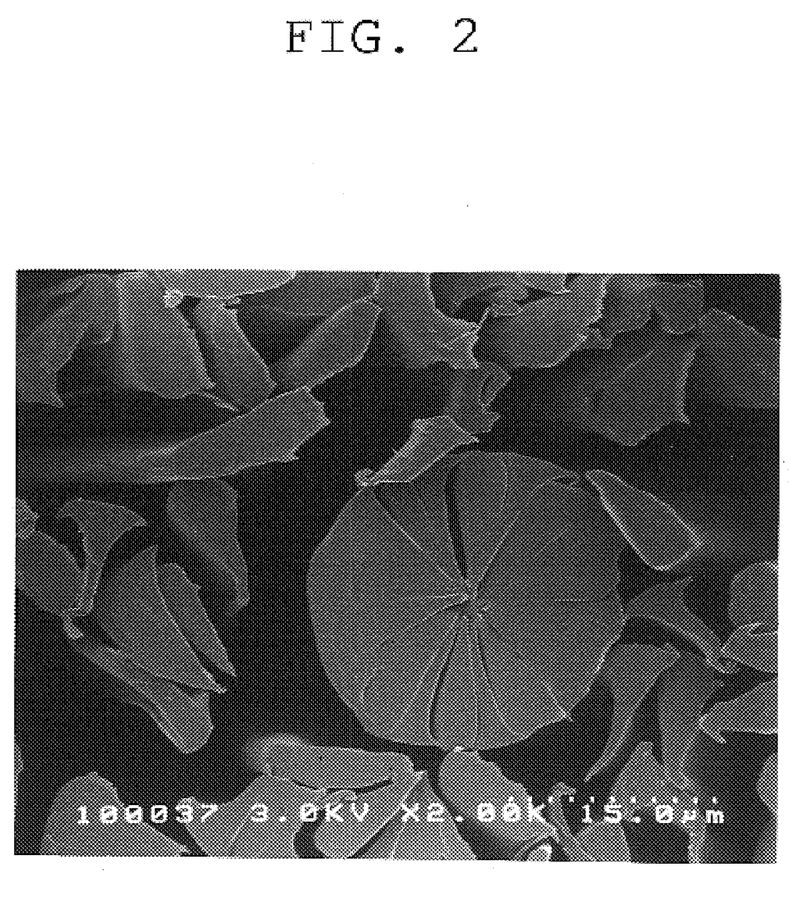
FIG. 2 is an electron micrographic sectional shape of the split type conjugated fiber of FIG. 1 after splitting with water stream, wherein one undivided split type conjugated fiber having an about circle sectional shape is seen in the vicinity of the center, and the divided plural split type conjugated fibers having about triangular sectional shapes are seen in the vicinity of the periphery.

FIG. 2 is an electron micrographic sectional shape of the above-mentioned split type conjugated fiber 1 after splitting with a water stream. In the near center of FIG. 2, one undivided split type conjugated fiber having an about circle sectional shape is seen, and the divided plural split type conjugated fibers having an about triangular sectional shape are seen in the vicinity of the periphery. In the case of the above-mentioned split type conjugated fiber 1, $D_L$ of the about triangular shape after division is about 10 $\mu$m, and $D_S$ is about 5 $\mu$m.

As the material of the above-mentioned split type conjugated fiber 1, the above-mentioned various fiber materials are exemplified, wherein the preferable combinations are polyester/polypropylene and polyester/polyethylene. The mixing ratio of these (polyester: polypropylene or polyethylene) is preferably 35:65–65:35, more preferably 40:60–60:40, most preferably 45:55–55:45 (wt %: wt %). When the mixing ratio is outside the above-mentioned range, the obtained split type conjugated fiber cannot be divided smoothly.

The resulting split type conjugated fiber divided in the above-mentioned manner is applied to a typical step, such as spun lace method, spun bond method, needle punch method and the like to finish into a nonwoven fabric. In view of the anchor effect with the adhesive plaster layer, feel and safety, one produced by a spun lace method is preferable.

The nonwoven fabric to be used in the present invention may contain 1 to 50, more preferably 2 to 30, undivided split type conjugated fibers in a 0.1 mm$^2$ section. The presence of undivided split type conjugated fibers in a nonwoven fabric improves shape retention of the nonwoven fabric, thereby enhancing the dimensional stability of a preparation. In addition, the stiffness becomes suitable, thereby improving the handling property of a preparation. When too many undivided split type conjugated fibers are contained in a 0.1 mm$^2$ section of a nonwoven fabric, the nonwoven fabric becomes too stiff, making it difficult for an intraoral adhesive preparation using the nonwoven fabric to follow uneven surfaces, which may cause considerable sensation of foreign matter upon application.

The nonwoven fabric to be used in the present invention has a thickness of preferably 300–600 μm, more preferably 350–500 μm, and a density of preferably 0.17–0.25 g/cm$^3$, more preferably 0.19–0.23 g/cm$^3$. As used herein, by the "thickness" is meant a thickness defined in JIS L1085 (Testing Methods for Nonwoven Interlining Fabrics) and by the "density" is meant a mass per unit volume calculated from the above-mentioned thickness and the mass defined in JIS L1085.

The intraoral adhesive preparation using a nonwoven fabric having the above-mentioned thickness and density has a suitable thickness and stiffness, and therefore, shows superior handling property when the adhesive sheet preparation is peeled off from the release liner or when applying the adhesive sheet preparation in the oral cavity. The sheet has a suitable high density, is not easily soaked with water such as saliva and the like, and does not permit easy occurrence of leakage and flow of a drug due to saliva during the intraoral application. Because the amount of the fiber on the surface of the nonwoven fabric, which adheres to an adhesive plaster layer, is appropriate, which makes a superior anchor effect of the adhesive plaster layer and the nonwoven fabric.

When the thickness of the nonwoven fabric is less than 300 μm, the handling property is degraded and water such as saliva etc. tends to sink into the fabric, and when it is thicker than 600 μm, it may cause considerable sensation of foreign matter upon application. When the density of the nonwoven fabric is lower than 0.17 g/cm$^3$, the handling property is degraded and water, such as saliva and the like, easily sinks in, and the anchor effect with an adhesive plaster layer is degraded. When it is higher than 0.25 g/cm$^3$, the fabric becomes too stiff. As a result, an intraoral adhesive preparation using this nonwoven fabric shows degraded followability to irregularities, and may cause considerable sensation of foreign matter upon application.

The drug to be used in the present invention is not particularly limited as long as it permits transmucosal administration in the oral cavity. Examples of the systemic drug include corticosteroids, analgesic inflammatory agent, hypnosedative, tranquilizer, antihypertensive agent, hypotensive diuretics, antibiotic, general anesthetic, antibacterial agent, antifungal agent, vitamin, coronary vasodilating agent, antihistaminic, antitussive, sex hormones, antidepressant, cerebral circulation improving agent, antiemetic drug, antitumor agent, biological medicine and the like. Examples of the local drug include local anesthetics such as lidocaine, dental antibiotics such as tetracycline hydrochloride, disinfectants such as cetylpyridinium chloride, agents for prophylaxis and therapy of intraoral infection such as chlorhexidine hydrochloride, antiphlogistics such as azulene, and the like. Preferably, at least one kind of local anesthetic selected from the group consisting of cocaine, procaine, chloroprocaine, tetracaine, benzocaine, lidocaine, mepivacaine, prilocaine, bupivacaine, dibucaine, propoxycaine, etidocaine, diclonine, oxybuprocaine, tecaine, amethocaine, propitocaine, piperocaine, quatacaine, butacaine, meprylcaine, amylocaine, isobucaine, tricaine, parethoxycaine, pyrrocaine, hexylcaine, metabutoxycaine, xylocaine, oxethazaine, pyridoxine, dimethisoquin, ethyl aminobenzoate, ethyl piperidinoacetyl aminobenzoate, benzyl alcohol, chlorobutanol and pharmacologically acceptable salts thereof is used, and more preferably, lidocaine, lidocaine hydrochloride, tetracaine and benzocaine are used.

The content of these drugs in the adhesive plaster layer is determined as appropriate according to the kind of the drug, object of administration and the like. It is generally about 1–80 wt %, preferably about 2–70 wt %. When the content is less than 1 wt %, the release of the drug in an amount effective for the treatment or prevention is not achieved, whereas when it exceeds 80 wt %, the adhesive property is degraded to lose sufficient adhesion, which poses a limit on the therapeutic or prophylactic effect and is economically disadvantageous.

The drug is contained in the state of being dissolved in an adhesive plaster layer, crystals precipitated therein by supersaturation, or being dispersed in an adhesive plaster layer, depending on drug efficacy (object of use). In this way, an intraoral adhesive preparation for the treatment and/or prevention of various diseases can be obtained.

The adhesive plaster layer is not subject to any particular limitation as long as it can substantially adhere to oral mucosa. It is formed using an adhesive wherein any polymer that shows pressure-sensitive adhesiveness at ordinary temperature is used as a base, and the like. A pressure-sensitive adhesive layer substantially insoluble in water or substantially water non-absorptive is preferable. In the present invention, by the "pressure-sensitive adhesive layer substantially insoluble in water or substantially water non-absorptive" is meant a pressure-sensitive adhesive layer formed using, as a main component, an adhesive polymer that shows solubility in water at 20° C. of not more than 5 wt % and shows pressure-sensitive adhesiveness at ordinary temperature and/or an adhesive polymer that shows absorption amount of water at 20° C. of not more than 5 wt % and shows pressure-sensitive adhesiveness at ordinary temperature. An adhesive (adhesive polymer) constituting such a pressure-sensitive adhesive layer substantially insoluble in water or substantially water non-absorptive is exemplified by acrylic adhesive; rubber adhesives such as styrene-isoprene-styrene block copolymer, styrene-butadiene-styrene block copolymer, polyisoprene, polyisobutylene, polybutadiene and the like; silicone adhesives such as silicone rubber, dimethylsiloxane-based silicone, diphenylsiloxane-based silicone and the like; vinyl ether adhesives such as poly(vinyl methyl ether), poly(vinyl ethyl ether), poly(vinyl isobutyl ether) and the like; vinyl ester adhesives such as vinyl acetate-ethylene copolymer and the like; polyester adhesives comprising a carboxylic acid component (e.g., dimethyl terephthalate, dimethyl isophthalate, dimethyl phthalate etc.) and a polyhydric alcohol component (e.g., ethylene glycol etc.) and the like; and the like. Of these, an acrylic adhesive is preferable in view of anchor effect with a nonwoven fabric, adhesion to mucosa, drug solubility, drug stability and the like.

The above-mentioned acrylic adhesive is obtained by copolymerizing alkyl (meth)acrylate as a main component with a functional monomer. The alkyl (meth)acrylate is exemplified by alkyl (meth)acrylate wherein the alkyl group thereof is a straight-chain alkyl group or branched-chain alkyl group having 4 to 13 carbon atoms, such as butyl, pentyl, hexyl, heptyl, octyl, 2-ethylhexyl, nonyl, decyl, undecyl, dodecyl, tridecyl and the like, wherein these can be used alone or in combination.

The functional monomer to be copolymerized with the above-mentioned alkyl (meth)acrylate has at least one unsaturated double bond involved in the copolymerization reaction in a molecule and a functional group in the side chain. Examples of such functional monomer include carboxyl group-containing monomers such as (meth)acrylic acid, itaconic acid, maleic acid, maleic anhydride and the like; hydroxyl group-containing monomers such as hydroxyethyl (meth)acrylate, hydroxypropyl (meth)acrylate and the like; sulfo group-containing monomers such as styrenesulfonic acid, allylsulfonic acid, sulfopropyl (meth)acrylate, (meth) acryloyloxynaphthalene sulfonic acid, acrylamide methylpropanesulfonic acid and the like; amino group-containing monomers such as aminoethyl (meth)acrylate, dimethylaminoethyl (meth)acrylate, tert-butylaminoethyl (meth)acrylate and the like; amide group-containing monomers such as (meth)acrylamide, dimethyl(meth)acrylamide, N-methylol (meth)acrylamide, N-methylolpropane(meth)acrylamide, N-vinylacetamide and the like; alkoxyl group-containing monomers such as methoxyethyl (meth)acrylate, ethoxyethyl (meth)acrylate, methoxyethylene glycol (meth) acrylate, methoxydiethylene glycol (meth)acrylate, methoxypolyethylene glycol (meth)acrylate, methoxypolypropylene glycol (meth)acrylate, tetrahydrofuryl (meth)acrylate and the like; and the like. Besides these, examples of the copolymerizable monomer include (meth) acrylonitrile, vinyl acetate, vinyl propionate, N-vinyl-2-pyrrolidone, methylvinylpyrrolidone, vinylpyridine, vinylpiperidone, vinylpyrimidine, vinylpiperazine, vinylpyrrole, vinylimidazole, vinylcaprolactam, vinyloxazole, vinylmorpholine and the like.

As far as the characteristics of the present invention are not adversely affected, alkyl (meth)acrylate having alkyl group having 1 to 3 or 14 or more carbon atoms may be copolymerized.

The acrylic adhesive in the present invention is preferably a copolymer of alkyl (meth)acrylate and (meth)acrylic acid, particularly a copolymer obtained by polymerizing alkyl (meth)acrylate (65–99 wt %) and (meth)acrylic acid (1–35 wt %), because they are particularly superior in pressure-sensitive adhesiveness and cohesion property as the adhesive property, release property of drug contained in an adhesive plaster layer and the like.

In the present invention, the adhesive polymer (adhesive) constituting the adhesive plaster layer is determined to achieve the object of administration of the drug. When administration in a short time is desired, an adhesive polymer superior in release of the contained drug is selected, and when administration for a long time is desired, an adhesive polymer capable of relatively sustained release of the contained drug is selected.

The above-mentioned adhesive plaster layer may contain various additives as necessary. Examples of the additive include tackifiers for improved adhesive property (e.g., rosin, denatured rosin, petroleum resin, polyterpene resin, polystyrene resin, polybutene resin, liquid polyisobutylene etc.), plasticizers (e.g., liquid paraffin, isopropyl myristate, isopropyl palmitate etc.), absorption improvers for higher solubility and diffusibility of drug in the adhesive plaster layer (e.g., glycols such as ethylene glycol, diethylene glycol, propylene glycol, triethylene glycol, polyethylene glycol, polypropylene glycol etc., fats and oils such as olive oil, castor oil, squalane, lanolin etc.), surfactants (e.g., sucrose fatty acid glycerin, stearyl alcohol, sorbitan trioleate, diethyl sebacate, sodium lauryl sulfate, polyoxyethylene hydrogenated castor oil, cholesterol etc.), fillers (e.g., kaolin, titanium oxide, talc, calcium carbonate, magnesium carbonate, silicate, silicic acid, aluminum hydrate, barium sulfate, calcium sulfate, magnesium aluminometasilicate etc.), and the like.

The production method of the intraoral adhesive preparation of the present invention is not subject to any particular limitation. For example, a drug, an adhesive polymer and the like are dissolved or dispersed in a solvent, the obtained solution or dispersion is applied onto at least one surface of a support, and dried to form an adhesive plaster layer on at least one surface of the support. It is also produced by applying the above-mentioned solution or dispersion onto a protective release liner, drying same to form an adhesive plaster layer on the release liner, and adhering the adhesive plaster layer on the release liner and a support. In this case, unexpected contact with and adhesion of the adhesive plaster layer to an instrument, container and the like during production, transport or storage can be prevented. It is also possible to protect the exposed surface of an adhesive plaster layer by applying a release liner until immediately before adhesion to oral mucosa, and separating the release liner when adhering to the oral mucosa to expose the adhesive plaster layer for adhesion, whereby degradation of the adhesive property of the adhesive plaster layer and deterioration of the drug can be prevented.

The material of the release liner is not subject to any particular limitation as far as it can be released easily from the adhesive plaster layer when in use. For example, synthetic resin film made from polyester, poly(vinyl chloride), poly(vinylidene chloride), poly(ethylene terephthalate) and the like, paper such as wood free paper, glassine paper and the like, a laminate film of wood free paper or glassine paper and the like and a polyolefin film, and the like, wherein the surface to be in contact with the adhesive plaster layer is covered with silicone resin, fluorocarbon resin and the like for release treatment, are used. The release liner has a thickness of generally 10–200 $\mu$m, preferably 50–100 $\mu$m.

The adhesive plaster layer has a thickness of generally 10 $\mu$m–200 $\mu$m, preferably 15 $\mu$m–150 $\mu$m.

The intraoral adhesive preparation of the present invention has a shorter diameter of preferably 0.5–1.5 cm, more preferably 0.7–1.3 cm, and a longer diameter of preferably 1–3 cm, more preferably 1.4–2.6 cm. As used herein, the "shorter diameter" and "longer diameter" mean the shortest diameter and the longest diameter, respectively, passing the center of gravity of an optional shape.

An intraoral adhesive preparation having the above-mentioned size is superior in handling property and fits well to an intraoral application site, such as gingiva and the like. When the adhesive sheet preparation has shorter and longer diameters that are smaller than the above-mentioned range, it cannot cover the application site sufficiently, cannot provide desired drug efficacy, but shows lower handling property. When the adhesive sheet preparation has shorter and longer diameters that are greater than the above-mentioned range, it does not stay on the application site and shows poor handling property.

The shape of the intraoral adhesive preparation of the present invention is not subject to any particular limitation as long as it can be adhered substantially. For example, it may be circle, ellipse, rectangle, square, triangle, hexagon and the like. Particularly it is preferably square from the aspects of production and use.

The intraoral adhesive preparation of the present invention preferably has a flex rigidity (by 45° cantilever method) as defined in JIS-L1085 of 15 mm–60 mm, more preferably 20 mm–50 mm, for the balance between handling property and feel during use. When the flex rigidity exceeds this range and is smaller, handling property tends to be degraded. For example, intraoral adhering of the sheet to a complicated and narrow space, as formed by dental part, tongue part and the like, tends to become difficult. When it is outside this range and is larger, a sense of foreign matter tends to occur easily upon application.

When the intraoral adhesive preparation of the present invention is prepared into an intraoral adhesive preparation containing a local drug, it is mainly adhered to gingiva to allow immediate expression of the drug efficacy. When the intraoral adhesive preparation of the present invention is prepared into an intraoral adhesive preparation containing a systemic drug, it is adhered to buccal mucosa, mucosa of inner surface of lips, hypoglottis, gingiva and the like, where the drug efficacy is maintained for tens of minutes to several hours. When the intraoral adhesive preparation containing a systemic drug of the present invention is adhered to mucosa of inner surface of upper lip or the outside of maxillary gingiva, the drug efficacy is maintained for a long time because contact with saliva is less, and the sheet is press-held by the labium and the gum.

The present invention is explained in detail by referring to examples. The present invention is not limited by these examples in any way. In the following description, "parts" means "parts by weight" and the thickness and density of a nonwoven fabric are measured according to the method defined in JIS-L1085.

Preparation of Adhesive Solution A

2-Ethylhexyl acrylate (95 parts) and acrylic acid (5 parts) were copolymerized in ethyl acetate under an inert gas atmosphere to prepare an adhesive solution A.

Preparation of Adhesive Solution B

2-Ethylhexyl acrylate (50 parts), 2-methoxyethyl acrylate (25 parts) and vinyl acetate (25 parts) were copolymerized in ethyl acetate under an inert gas atmosphere to prepare an adhesive solution B.

Preparation of Adhesive Solution C

2-Methoxyethyl acrylate (65 parts), vinylpyrrolidone (30 parts) and acrylic acid (5 parts) were copolymerized in ethyl acetate under an inert gas atmosphere to prepare an adhesive solution C.

Preparation of Rubber Polymer Solution D

Polyisobutylene (50 parts, viscosity-average molecular weight:120,000), polyisobutylene (30 parts, viscosity-average molecular weight:60,000) and alicyclic petroleum resin (20 parts, tackifier, softening point:100° C.) were homogeneously mixed in hexane to prepare a rubber polymer solution D.

EXAMPLE 1

Figure 3:
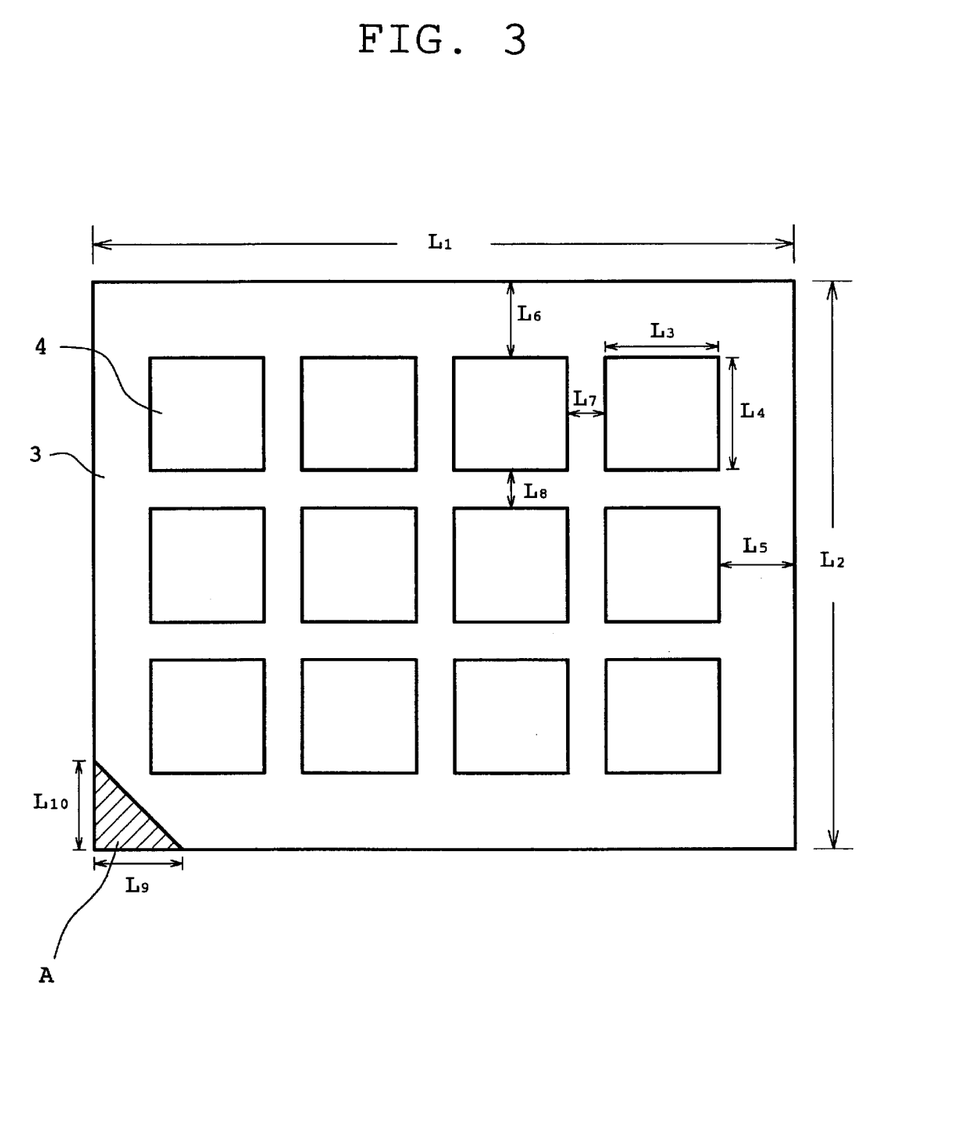
FIG. 3 schematically shows one embodiment of the intraoral adhesive preparation of the present invention.

Lidocaine (60 parts) was added to adhesive solution A (40 parts, solids) and mixed for dissolution. The obtained solution was applied to a polyester film (release liner, thickness 75 μm) that underwent a release treatment to achieve a thickness after drying of about 20 μm, and dried to give an adhesive plaster layer. The adhesive plaster layer was adhered to a nonwoven fabric (thickness 420 μm, density:0.21 g/cm$^3$, number of undivided split type conjugated fibers 12 fibers/0.1 mm$^2$ section) prepared by interlacing a 20-split split type conjugated fiber made of polypropylene and polyester (polypropylene content:55 wt %, polyester content:45 wt %; fiber diameter:20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in a square having a shorter diameter of about 1 cm and a longer diameter of about 1.4 cm, as shown in FIG. 3, which was placed on a release liner 3, whereby plural test pieces 4 were obtained. In FIG. 3, L1=63 mm, L2=50 mm, L3=L4=10 mm, L5=L6=7 mm, L7=L8=3 mm and L9=L10=7 mm.

COMPARATIVE EXAMPLE 1

Lidocaine (60 parts) was added to adhesive solution A (40 parts, solids) and mixed for dissolution. The obtained solution was applied to a polyester film (release liner, thickness 75 μm) that underwent a release treatment to achieve a thickness after drying of about 20 μm, and dried to give an adhesive plaster layer. The adhesive plaster layer was adhered to a polyethylene terephthalate (PET) film (thickness 12 μm) to give an intraoral medical adhesive sheet having a release liner. The obtained sheet was punched out in a square having a shorter diameter of about 1 cm and a longer diameter of about 1.4 cm, as shown in FIG. 3, which was placed on a release liner 3, whereby plural test pieces 4 were obtained.

COMPARATIVE EXAMPLE 2

Lidocaine (60 parts) was added to adhesive solution A (40 parts, solids) and mixed for dissolution. The obtained solution was applied to a polyester film (release liner, thickness 75 μm) that underwent a release treatment to achieve a thickness after drying of about 20 μm, and dried to give an adhesive plaster layer. The adhesive plaster layer was adhered to a spun laced stretch nonwoven fabric (thickness 700 μm, density:0.14 g/cm$^3$) made of a polyester fiber having a fiber diameter of 20 μm to give an intraoral medical adhesive sheet having a release liner. The obtained adhesive sheet preparation was punched out in a square having a shorter diameter of about 1 cm and a longer diameter of about 1.4 cm, as shown in FIG. 3, which was placed on a release liner 3, whereby plural test pieces 4 were obtained.

Comparative Example 3

Lidocaine (60 parts) was added to adhesive solution A (40 parts, solids) and mixed for dissolution. The obtained solution was applied to a polyester film (release liner, thickness 75 μm) that underwent a release treatment to achieve a thickness after drying of about 20 μm, and dried to give an adhesive plaster layer. The adhesive plaster layer was adhered to a spun laced nonwoven fabric (thickness 325 μm, density:0.23 g/cm$^3$) made of a polyester fiber having a fiber diameter of 4 μm and a circular fiber cross-section to give an intraoral medical adhesive sheet having a release liner. The obtained sheet was punched out in a square having a shorter diameter of about 1 cm and a longer diameter of about 1.4 cm, as shown in FIG. 3, which was placed on a release liner 3, whereby plural test pieces 4 were obtained.

Evaluation of Practical Use

The test pieces obtained in Example 1, Comparative Examples 1, 2 and 3 were applied to the inside of the maxillary gingiva gently dried with absorbent cotton in advance. The test pieces were evaluated by easiness of peeling off from the release liner, handling property in the oral cavity, adhesion to the application site, feeling during adhesion, bitterness during use, easiness of peeling off from the application site, glue remainder upon peeling off, and pharmacological effect according to the following methods using 5 volunteers. The evaluation results are shown in Table 1. In Table 1, average evaluation points of 5 volunteers are shown.

Easiness of Peeling Off of Test Piece From Release Liner

As shown in FIG. 3, each test piece placed on a release liner was held at point A with thumb and index finger of left hand and peeled off with tweezers. The handling property then was evaluated according to the following numerical criteria.
  0: difficult to peel off
  1: rather difficult to peel off
  2: easy to peel off Handling Property in Oral Cavity Each test piece held with tweezers was adhered to the maxillary gingiva of a different volunteer and the handling property then in the oral cavity was evaluated according to the following numerical criteria.
  0: difficult to handle
  1: rather difficult to handle
  2: easy to handle Adhesion to the Application Site Adhesion of each test piece to the application site inside the maxillary gingiva was evaluated according to the following numerical criteria.
  0: insufficient adhesion with a part being loose
  1: almost sufficient adhesion with periphery being slightly loose
  2: sufficient adhesion Feeling During Adhesion Uncomfortableness during adhesion was evaluated according to the following numerical criteria.
  0: uncomfortableness felt
  1: slight uncomfortableness felt
  2: almost no uncomfortableness felt Bitterness During Use The support of the test piece was tasted with the tip of the tongue wet with saliva every 30 seconds after adhesion to evaluate the bitterness due to the drug and evaluated according to the following numeral criteria.
  0: bitterness felt within 1 minute after adhesion
  1: bitterness felt after 1 minute and within 3 minutes from adhesion
  2: bitterness not felt even after 3 minutes from adhesion Easiness of Peeling Off of Test Piece From Application Site At 3 minutes after adhesion, each test piece was peeled off with tweezers. The handling property then was evaluated according to the following numerical criteria.
  0: difficult to peel off
  1: rather difficult to peel off
  2: easy to peel off Glue Remainder Upon Peeling Off The test piece was peeled off and the remainder of the adhesive plaster layer at the application site of the test piece was evaluated according to the following numeral criteria.
  0: remainder in 10% or more of adhesion area
  1: remainder in less than 10% of adhesion area
  2: no remainder Pharmacological Effect The test piece was peeled off and the application site was stimulated with a syringe needle. The anesthetic effect was evaluated according to the following numeral criteria.
  0: pain was felt
  1: slight pain was felt
  2: pain was not felt

TABLE 1

| Evaluation items | Ex. 1 | Com. Ex. 1 | Com. Ex. 2 | Com. Ex. 3 |
|---|---|---|---|---|
| easiness of peeling off of test piece from release liner | 2.0 | 0.0 | 1.6 | 1.4 |
| handling property in oral cavity | 2.0 | 0.6 | 1.0 | 0.8 |
| adhesion to the application site | 2.0 | 0.4 | 2.0 | 2.0 |
| feeling during adhesion | 2.0 | 0.4 | 2.0 | 2.0 |
| bitterness during use | 2.0 | 2.0 | 1.4 | 0.6 |
| easiness of peeling off of test piece from application site | 2.0 | 0.2 | 1.8 | 1.4 |
| glue remainder upon peeling off | 2.0 | 2.0 | 0.2 | 2.0 |
| pharmacological effect | 2.0 | 1.8 | 2.0 | 2.0 |

Permeability of Saliva

The adhesive sheet preparations of Example 1, Comparative Examples 1, 2 and 3 (of the type shown in FIG. 3 having one 1 cm×1 cm piece) were placed on the bottom of the beaker with the release liner facing downward and heated to 37° C. One drop (about 25 mg) of saliva of male adult, which was maintained at 37° C., was dropped in the center of the support, and the beaker was sealed and maintained at 37° C. The size of the saliva at 30 minutes after dripping and during standing was observed and permeability of the saliva was evaluated. The results are shown in Table 2.

TABLE 2

| | Ex. 1 | Com. Ex. 1 | Com. Ex. 2 | Com. Ex. 3 |
|---|---|---|---|---|
| Size (height × maximum width when seen from above) of saliva drop (mm) | 2.3 × 4.2 | 2.1 × 4.5 | All soaked in 20 min | All soaked in immediately after dripping |
| Permeability of saliva | Low permeability | No permeation | High permeability | High permeability |

From Tables 1 and 2, it is evident that the adhesive sheet preparation of Example 1 showed superior results in all evaluation items and showed low saliva permeability. In contrast, the adhesive sheet preparation of Comparative Example 1 comprising a PET film as a support showed inferior results in easiness of peeling off of test piece from release liner, handling property in oral cavity, adhesion to the application site, feeling during adhesion and easiness of peeling off of test piece from application site. The adhesive sheet preparations of Comparative Examples 2 and 3 without a nonwoven fabric made of split type conjugated fiber as a support showed inferior results in the evaluation of handling property in oral cavity, bitterness during use, and glue remainder upon peeling off, but showed high permeability of saliva.

EXAMPLE 2

Lidocaine (60 parts) was added to adhesive solution A (40 parts, solids) and mixed for dissolution. The obtained solution was applied to a polyester film (release liner, thickness 75 μm) that underwent a release treatment to achieve a thickness after drying of about 20 μm, and dried to give an adhesive plaster layer. The adhesive plaster layer was adhered to a nonwoven fabric (thickness 330 μm, density:0.18 g/cm³, no undivided split type conjugated fiber) prepared by interlacing a 16-split split type conjugated fiber made of polyethylene resin having hydrophilic group and polypropylene (polyethylene resin content: 50 wt %, polypropylene content: 50 wt %; fiber diameter: 20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in a square having a shorter diameter of about 1 cm and a longer diameter of about 1.4 cm, whereby a test piece as shown in FIG. 3 was obtained.

EXAMPLE 3

Azulene (5 parts) was added to adhesive solution B (95 parts, solids) and mixed for dissolution. The obtained solution was applied to a polyester film (release liner, thickness 75 μm) that underwent a release treatment to achieve a thickness after drying of about 40 μm, and dried to give an adhesive plaster layer. The adhesive plaster layer was adhered to a nonwoven fabric (thickness 420 μm, density:0.21 g/cm³, number of undivided split type conjugated fibers 12 fibers/0.1 mm² section) prepared by interlacing a 20-split split type conjugated fiber made of polypropylene and polyester (polypropylene content: 55 wt %, polyester content: 45 wt %; fiber diameter: 20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in an ellipse having a shorter diameter of about 1 cm and a longer diameter of about 1.5 cm, whereby a test piece as shown in FIG. 3 was obtained.

EXAMPLE 4

Isopropyl myristate (plasticizer, 25 parts) and diazepam (tranquilizer, 5 parts) were added to adhesive solution C (70 parts, solids) and mixed for dissolution. The obtained solution was applied to a polyester film (release liner, thickness 75 μm) that underwent a release treatment to achieve a thickness after drying of about 30 μm, and dried to give an adhesive plaster layer. The adhesive plaster layer was adhered to a nonwoven fabric (thickness 420 μm, density:0.21 g/cm³, number of undivided split type conjugated fibers 12 fibers/0.1 mm² section) prepared by interlacing a 20-split split type conjugated fiber made of polypropylene and polyester (polypropylene content: 55 wt %, polyester content: 45 wt %; fiber diameter: 20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in a circle having a diameter of about 1.2 cm, whereby a test piece as shown in FIG. 3 was obtained.

EXAMPLE 5

Isopropyl myristate (plasticizer, 20 parts) and cimetidine (anti-gastric tumor agent, 10 parts) were added to rubber polymer solution D (70 parts, solids) and mixed for dissolution. The obtained solution was applied to a polyester film (release liner, thickness 75 μm) that underwent a release treatment to achieve a thickness after drying of about 40 μm, and dried to give an adhesive plaster layer. The adhesive plaster layer was adhered to a nonwoven fabric (thickness 420 μm, density:0.21 g/cm³, number of undivided split type conjugated fibers 12 fibers/0.1 mm² section) prepared by interlacing a 20-split split type conjugated fiber made of polypropylene and polyester (polypropylene content: 55 wt %, polyester content: 45 wt %; fiber diameter: 20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in a rectangle having a shorter diameter of about 1 cm and a longer diameter of about 2 cm, whereby a test piece as shown in FIG. 3 was obtained.

EXAMPLE 6

Tetracaine (5 parts) was added to adhesive solution B (95 parts, solids) and mixed for dissolution. The obtained solution was applied to a polyester film (release liner, thickness 75 μm) that underwent a release treatment to achieve a thickness after drying of about 40 μm, and dried to give an adhesive plaster layer. The adhesive plaster layer was adhered to a nonwoven fabric (thickness 330 μm, density:0.18 g/cm³, no undivided split type conjugated fibers) prepared by interlacing a 16-split split type conjugated fiber made of polyethylene resin having hydrophilic group and polypropylene (polyethylene resin content: 50 wt %, polypropylene content: 50 wt %; fiber diameter: 20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in an isosceles triangle having a shorter diameter of about 0.6 cm and a longer diameter of about 1 cm, whereby a test piece as shown in FIG. 3 was obtained.

EXAMPLE 7

Isopropyl myristate (plasticizer, 20 parts) and lidocaine hydrochloride (10 parts) were added to adhesive solution C (70 parts, solids) and mixed for dissolution. The obtained solution was applied to a polyester film (release liner, thickness 75 μm) that underwent a release treatment to achieve a thickness after drying of about 30 μm, and dried to give an adhesive plaster layer. The adhesive plaster layer was adhered to a nonwoven fabric (thickness 330 μm, density:0.18 g/cm³, no undivided split type conjugated fibers) prepared by interlacing a 16-split split type conjugated fiber made of polyethylene resin having hydrophilic group and polypropylene (polyethylene resin content: 50 wt %, polypropylene content: 50 wt %; fiber diameter: 20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in a square having a shorter diameter of about 1 cm and a longer diameter of about 1.4 cm, whereby a test piece as shown in FIG. 3 was obtained.

EXAMPLE 8

Isopropyl myristate (plasticizer, 30 parts) and benzocaine (10 parts) were added to rubber polymer solution D (60 parts, solids) and mixed for dispersion. The obtained dispersion was applied to a polyester film (release liner, thickness 75 μm) that underwent a release treatment to achieve a thickness after drying of about 40 μm, and dried to give an adhesive plaster layer. The adhesive plaster layer was adhered to a nonwoven fabric (thickness 330 μm, density:0.18 g/cm³, no undivided split type conjugated fibers) prepared by interlacing a 16-split split type conjugated fiber made of a polyethylene resin having a hydrophilic group and a polypropylene (polyethylene resin content: 50 wt %, polypropylene content: 50 wt %; fiber diameter: 20 μm) upon division with high pressure water stream (fiber sectional shape after splitting: about triangular shape, $D_L$=10 μm, $D_S$=5 μm, $D_L/D_S$=2) to give an intraoral medical adhesive sheet having a release liner. The obtained adhesive sheet preparation was punched out in a square having a shorter diameter of about 1 cm and a longer diameter of about 1.4 cm, whereby a test piece as shown in FIG. 3 was obtained.

The test pieces obtained in Examples 2–8 were applied to the inside of the maxillary gingiva gently dried with absorbent cotton in advance. The test pieces were evaluated by easiness of peeling off from the release liner, handling property in the oral cavity, adhesion to the application site, feeling during adhesion, bitterness during use, easiness of peeling off from the application site, glue remainder upon peeling off, and pharmacological effect (except Examples 3–5) according to the above-mentioned methods using 5 volunteers. The evaluation results are shown in Table 3. In Table 3, average evaluation points of 5 volunteers are shown.

TABLE 3

|  | Ex. 2 | Ex. 3 | Ex. 4 | Ex. 5 | Ex. 6 | Ex. 7 | Ex. 8 |
|---|---|---|---|---|---|---|---|
| easiness of peeling off of test piece from the release liner | 2.0 | 2.0 | 2.0 | 2.0 | 2.0 | 2.0 | 2.0 |
| handling property in oral cavity | 2.0 | 2.0 | 2.0 | 2.0 | 2.0 | 2.0 | 2.0 |
| adhesion to the application site | 2.0 | 2.0 | 2.0 | 2.0 | 2.0 | 2.0 | 2.0 |
| feeling during adhesion | 2.0 | 2.0 | 2.0 | 2.0 | 2.0 | 2.0 | 2.0 |
| bitterness during use | 2.0 | 2.0 | 2.0 | 2.0 | 2.0 | 2.0 | 2.0 |
| easiness of peeling off of test piece from application site | 2.0 | 2.0 | 2.0 | 2.0 | 2.0 | 2.0 | 2.0 |
| glue remainder upon peeling off | 2.0 | 2.0 | 2.0 | 2.0 | 2.0 | 2.0 | 2.0 |
| pharmacological effect | 2.0 | — | — | — | 2.0 | 2.0 | 2.0 |

From Table 3, it is evident that the adhesive sheet preparations of Examples 2–8 showed superior results in all evaluation items.

According to the present invention, an intraoral adhesive preparation is provided, which comprises a support made of a nonwoven fabric mainly made of split type conjugated fibers, and an adhesive plaster layer containing a drug, which is formed on the support, wherein the split type conjugated fiber has an about triangular sectional shape after splitting, where the about triangle has the longest diameter ($D_L$) of 5 μm–15 μm, and the longest line segment ($D_S$) that vertically crosses the longest diameter of 2 μm–10 μm. According to the present invention, an intraoral adhesive preparation superior in an anchor effect of the support and the adhesive plaster layer, flexibility, followability to an area with uneven surfaces, thus obliterating uncomfortableness such as stiffness and the like, handling property in a narrow place as in the oral cavity, and prevention of leakage and flow of the drug due to saliva can be provided.

This application is based on a patent application No. 2000-263623 filed in Japan, the content of which is hereby incorporated by reference.

What is claimed is:

1. An intraoral adhesive preparation comprising a support made of a nonwoven fabric mainly made of split type conjugated fibers, and an adhesive plaster layer containing a drug, which is formed on the support, wherein the split type conjugated fiber has an about triangular sectional shape after splitting, where the about triangle has the longest diameter ($D_L$) of 5 μm–15 μm, and the longest line segment ($D_S$) that vertically crosses the longest diameter of 2 μm–10 μm.

2. The intraoral adhesive preparation of claim 1, which has a $D_L/D_S$ ratio of 1.5–2.5.

3. The intraoral adhesive preparation of claim 1, which is obtained by splitting a conjugated fiber consisting of at least two kinds of fiber materials combined radially from the about center of the section, wherein the number of split is not less than 16.

4. The intraoral adhesive preparation of claim 1, wherein the nonwoven fabric contains 1 to 50 undivided split type conjugated fibers in a 0.1 mm² section.

5. The intraoral adhesive preparation of claim 1, wherein the nonwoven fabric has a thickness of 300–600 μm, and a density of 0.17–0.25 g/cm³.

6. The intraoral adhesive preparation of claim 1, which has a shorter diameter of 0.5–1.5 cm and a longer diameter of 1–3 cm.

* * * * *